United States Patent [19]
Ishii et al.

[11] Patent Number: 6,111,128
[45] Date of Patent: Aug. 29, 2000

[54] PROCESSES FOR PRODUCING α-CYANOHYDRIN ESTERS AND α-HYDROXY ACIDS

[75] Inventors: Yasutaka Ishii, Takatsuki; Tatsuya Nakano, Himeji, both of Japan

[73] Assignee: Daicel Chemical Industries, Ltd., Osaka, Japan

[21] Appl. No.: 09/213,424

[22] Filed: Dec. 17, 1998

[30] Foreign Application Priority Data

Dec. 22, 1997 [JP] Japan ................................. 9-353395

[51] Int. Cl.$^7$ ........................ C07C 263/00; C07C 249/00
[52] U.S. Cl. ............................... 558/341; 558/351
[58] Field of Search ..................... 558/341, 351

[56] References Cited

U.S. PATENT DOCUMENTS

4,113,763  9/1978  Norton .
4,299,776  11/1981  Hatch, III .

FOREIGN PATENT DOCUMENTS

1540632  2/1979  United Kingdom .

OTHER PUBLICATIONS

J. March, *Advanced Organic Chemistry,* 4th Edition, XP002097784, pp.397–398 (1992).

*Primary Examiner*—Joseph McKane
*Assistant Examiner*—Joseph Murray
*Attorney, Agent, or Firm*—Birch, Stewart, Kolasch & Birch, LLP

[57] ABSTRACT

In the presence of a metal catalyst such as a samarium compound, an enol ester compound shown by the formula (1) is reacted with a carbonyl compound shown by the formula (3) and a cyanogenation agent to produce an α-cyanohydrin ester shown by the formula (4):

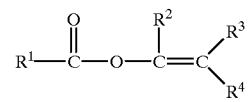

(1)

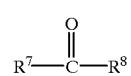

(3)

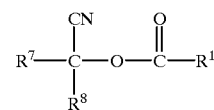

(4)

wherein $R^1$, $R^7$, and $R^8$ are the same or different from each other, each representing a non-reactive atom or a non-reactive organic group; $R^2$, $R^3$, and $R^4$ are the same or different from each other, each representing a hydrogen atom or an alkyl group having 1 to 5 carbon atoms.

By hydrolyzing the obtained compound, the corresponding α-hydroxy acid or a salt thereof can be obtained. According to the above processes, an α-cyanohydrin ester and an α-hydroxy acid can be obtained in high yields.

15 Claims, No Drawings

PROCESSES FOR PRODUCING α-CYANOHYDRIN ESTERS AND α-HYDROXY ACIDS

FIELD OF THE INVENTION

The present invention relates to processes for producing an α-cyanohydrin ester and an α-hydroxy acid, or salts thereof using an enol ester compound or an oxime ester compound, a carbonyl compound and a cyanogenation agent.

BACKGROUND OF THE INVENTION

α-hydroxy acids are very useful compounds as precise fine chemicals such as medicines and agricultural chemicals, or intermediates thereof.

As a process for producing α-hydroxy acids, there has been known a process which comprises reacting a carbonyl compound such as an aldehyde with a cyanogenation agent such as hydrogen cyanide to produce the corresponding α-cyanohydrin compound, then hydrolyzing the obtained α-cyanohydrin compound. In this process, however, since the cyanogenation reaction is reversible, it is generally difficult to obtain the corresponding α-cyanohydrin compound (particularly, an α-cyanohydrin compound derived from an aldehyde) in high yield. Moreover, since the obtained α-cyanohydrin compound tends to decompose into the carbonyl compound and hydrogen cyanide by the hydrolysis, it is difficult to produce an α-hydroxy acid in high yield.

SUMMARY OF THE INVENTION

It is, therefore, an object of the present invention to provide a process for producing a highly stable α-cyanohydrin ester useful as a precursor of an α-hydroxy acid in high yield.

It is another object of the present invention to provide a process for producing an α-hydroxy acid or a salt thereof in high yield.

A further object of the present invention is to provide a process for producing an α-hydroxy acid which is general-purpose and of broader applicability, or a salt thereof.

The inventors of the present invention did intensive investigation, and found that the reaction of an enol ester compound or an oxime ester compound with a carbonyl compound and a cyanogenation agent in the presence of a metal catalyst provides the corresponding α-cyanohydrin ester in high yield and that the corresponding α-hydroxy acid or a salt thereof can be efficiently derived from the α-cyanohydrin ester by hydrolysis. The present invention was accomplished based on the above findings.

That is to say, the present invention provides a process for producing an α-cyanohydrin ester derivative, which comprises, in the presence of a metal catalyst, reacting an enol ester compound shown by the formula (1):

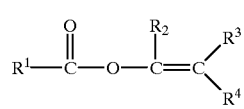

(1)

wherein $R^1$ represents a non-reactive atom or a non-reactive organic group; $R^2$, $R^3$, and $R^4$ are the same or different from each other and each represents a hydrogen atom or an alkyl group having 1 to 5 carbon atoms; and $R^2$, $R^3$, and $R^4$, together with 1 or 2 adjacent carbon atoms, may bond together to form a ring or an oxime ester compound shown by the formula (2):

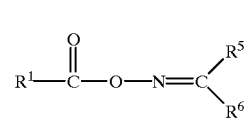

(2)

wherein $R^5$ and $R^6$ are the same or different from each other and each represents a non-reactive atom or a non-reactive organic group; $R^5$ and $R^6$, together with the adjacent carbon atom, may bond together to form a ring; and $R^1$ has the same meaning as defined above with a carbonyl compound shown by the formula (3):

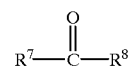

(3)

wherein $R^7$ and $R^8$ are the same or different from each other and each represents a non-reactive atom or a non-reactive organic group; and $R^7$ and $R^8$, together with the adjacent carbon atom, may bond together to form a ring and a cyanogenation agent to form an α-cyanohydrin ester shown by the formula (4):

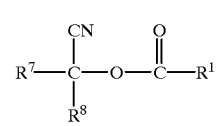

(4)

wherein $R^1$, $R^7$, and $R^8$ have the same meanings as defined above.

As the metal catalyst, for example, transition metal compounds may be used. $R^1$ includes, e.g., hydrogen atom, $C_{1-10}$alkyl groups, $C_{2-10}$alkenyl groups, $C_{3-10}$cycloalkyl groups and $C_{6-10}$aryl groups. $R^2$ to $R^4$ each represents, e.g., a hydrogen atom or a $C_{1-3}$alkyl group. $R^5$ and $R^6$ include $C_{1-10}$alkyl groups, $C_{3-10}$cycloalkyl groups and $C_{6-10}$aryl groups, etc. $R^5$ and $R^6$, together with the adjacent carbon atom, may bond together to form, e.g., an about 3 to 20-membered cycloalkane ring. As the cyanogenation agent, there may be exemplified hydrogen cyanide, metal cyanides, cyanohydrin compounds, and acyl cyanides.

Further, the present invention provides a process for producing an α-hydroxy acid shown by the formula (5):

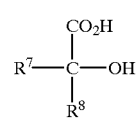

(5)

wherein $R^7$ and $R^8$ have the same meanings as defined above or a salt thereof which comprises hydrolyzing an α-cyanohydrin ester produced according to the above process and shown by the formula (4).

DETAILED DESCRIPTION OF THE INVENTION

[Metal catalyst]

The metal catalyst includes simple substances and compounds of various metal elements, and may be used singly or as a combination thereof. As the metal elements, there may be exemplified the group 2A elements of the Periodic Table of Elements (e.g., magnesium Mg, calcium Ca, strontium Sr, barium Ba), transition metal elements, and the group 3B elements of the Periodic Table of Elements (e.g., boron B, aluminum Al). In the present specification, boron B is also included as a metal element.

As the transition metal elements, there may be exemplified the group 3A elements [rare earth metal elements (e.g., scandium Sc, yttrium Y, lanthanoid elements (lanthanum La, cerium Ce, praseodymium Pr, neodymium Nd, promethium Pm, samarium Sm, europium Eu, gadolinium Gd, terbium Tb, dysprosium Dy, holmium Ho, erblum Er, thulium Tm, ytterbium Yb, lutetium Lu), actinoid elements (e.g., actinium Ac)], the group 4A elements (e.g., titanium Ti, zirconium Zr, hafnium Hf), the group 5A elements (e.g., vanadium V, niobium Nb, tantalum Ta), the group 6A elements (e..g, chromium Cr, molybdenum Mo, tungsten W), the group 7A elements (e.g., manganese Mn, technetium Tc, rhenium Re), the group 8 elements (e.g., iron Fe, ruthenium Ru, osmium Os, cobalt Co, rhodium Rh, iridium Ir, nickel Ni, palladium Pd, platinum Pt), the group 1B elements (e.g., copper Cu, silver Ag, gold Au), and the group 2B elements (e.g., zinc Zn, cadmium Cd) of the Periodic Table of Elements.

Preferred elements as a component of the metal catalyst include transition metal elements (e.g., rare earth metal elements such as lanthanoid elements, the group 3A elements such as actinoid elements, the group 4A elements, the group 5A elements, the group 6A elements, the group 7A elements, the group 8 elements, the group 1B elements, the group 2B elements) and the group 3B elements of the Periodic Table of Elements.

Compounds comprising a metal element include hydroxides, metal oxides (e.g., double oxides or oxygen acids, or salts thereof), organic acid salts, inorganic acid salts, halides, coordination compounds (complex) containing any of the metal elements mentioned above, and polyacids (e.g., heteropolyacids and isopolyacids), or salts thereof. As for the metal compounds, the valence of their elements is not particularly restricted, and may be about 2 to 6.

As the hydroxides, there may be exemplified $Sm(OH)_2$, $Sm(OH)_3$, $Mn(OH)_2$, $MnO(OH)$, $Fe(OH)_2$, $Fe(OH)_3$, and other corresponding metal hydroxides. As the metal oxides, there may be exemplified $SmO_2$, $SmO_3$, $TiO_2$, $ZrO_2$, $V_2O_3$, $V_2O_5$, $CrO$, $Cr_2O_3$, $MoO_3$, $MnO$, $Mn_3O_4$, $Mn_2O_3$, $MnO_2$, $Mn_2O_7$, $FeO$, $Fe_2O_3$, $Fe_3O_4$, $RuO_2$, $RuO_4$, $CoO$, $CoO_2$, $Co_2O_3$, $RhO_2$, $Rh_2O_3$, $Cu_2O_3$, and other corresponding metal oxides. As the double oxides or oxygen acids, or salts thereof, there may be exemplified $MnAl_2O_4$, $MnTiO_3$, $LaMnO_3$, $K_2Mn_2O_5$, $CaO \cdot xMnO_2(x=0.5, 1, 2, 3, 5)$, manganates [e.g., manganates (V) such as $Na_3MnO_4$, and $Ba_3[MnO_4]_2$; manganates (VI) such as $K_2MnO_4$, $Na_2MnO_4$, and $BaMnO_4$; and permanganates such as $KMnO_4$, $NaMnO_4$, $LiMnO_4$, $NH_4MnO_4$, $CsMnO_4$, $AgMnO_4$, $Ca(MnO_4)_2$, $Zn(MnO_4)_2$, $Ba(MnO_4)_2$, $Mg(MnO_4)_2$, and $Cd(MnO_4)_2$; molybdic acid; tungstic acid; and other corresponding metal double oxides or oxygen acids, or salts thereof.

As organic acid salts, there may be exemplified salts of organic acids such as organic carboxylic acid (e.g., monocarboxylic acids such as formic acid, acetic acid, trichloroacetic acid, trifluoroacetic acid, propionic acid, butyric acid, valeric acid, naphthenic acid, and stearic acid; polycarboxylic acids such as oxalic acid and maleic acid); hydroxycarboxylic acids. (e.g., glycolic acid, lactic acid, malic acid, tartaric acid, citric acid), thiocyanic acid, sulfonic acids (e.g., alkylsulfonic acids such as methanesulfonic acid, trichloromethanesulfonic acid, trifluoromethanesulfonic acid, and ethanesulfonic acid; arylsulfonic acids such as benzenesulfonic acid and p-toluenesulfonic acid). As inorganic acid salts, there may be exemplified nitrates, sulfates, phosphates, carbonates, and perchlorates. Concrete examples of organic acid salts or inorgnaic acid salts are samarium (II) acetate, samarium (III) acetate, cobalt acetate, manganese acetate, cobalt propionate, manganese propionate, cobalt naphthenate, manganese naphthenate, cobalt stearate, manganese stearate, manganese thiocyanate, samarium (II) trichloroacetate, samarium (III) trichloroacetate, samarium (II) trifluoroacetate, samarium (III) trifluoroacetate, samarium (II) trifluoromethanesulfonate (i.e., samarium (II) triflate), samarium (III) trifluoromethanesulfonate (i.e., samarium (III) triflate), samarium (II) nitrate, cobalt nitrate, iron nitrate, manganese nitrate, nickel nitrate, copper nitrate, samarium (II) sulfate, cobalt sulfate, iron sulfate, manganese sulfate, samarium (II) phosphate, cobalt phosphate, iron phosphate, manganese phosphate, samarium (II) carbonate, iron carbonate, manganese carbonate, iron perchlorate, and other corresponding metal organic acid salts or inorganic acid salts.

Halides include fluorides, chlorides, bromides and iodides. There may be mentioned, for example, halides such as chlorides [e.g., $SmCl_2$, $SmCl_3$, $TiCl_2$, $TiCl_4$, $ZrCl_2$, $ZrOCl_2$, $VCl_3$, $VOCl_2$, $MOCl_3$, $MnCl_2$, $MnCl_3$, $FeCl_2$, $FeCl_3$, $RuCl_3$, $COCl_2$, $RhCl_2$, $RhCl_3$, $NiCl_2$, $PdCl_2$, $PtCl_2$, $CuCl$, $CuCl_2$, $AlC_3$], the corresponding fluorides, bromides and iodides (e.g., $SmF_2$, $SmF_3$, $SmBr_2$, $SmBr_3$, $SmI_2$, $SmI_3$, $MnF_2$, $MnBr_2$, $MnF_3$, $FeF_2$, $FeF_3$, $FeBr_2$, $FeBr_3$, $FeI_2$, $CuBr$, $CuBr_2$), double halides such as $M^1MnCl_3$, $M^1{}_2MnCl_4$, $M^1{}_2MnCl_5$, $M^1{}_2MnCl_6$ ($M^1$ indicates a monovalent metal), and other corresponding metal halides.

As a ligand forming a complex, there may be exemplified hydroxo (OH), alkoxy groups such as methoxy, ethoxy, propoxy, and butoxy groups; acyl groups such as acetyl, and propionyl groups; alkoxycarbonyl groups such as methoxycarbonyl (acetato) and ethoxycarbonyl groups; acetylacetonato, cyclopentadienyl, $C_{1-4}$alkyl-substituted dicyclopentadienyls (e.g., pentamethylcyclopentadienyl); halogen atoms such as chlorine and bromine; CO; CN; oxygen atom; $H_2O$ (aquo); phosphorous compounds such as phosphines (e.g., triarylphosphines such as triphenylphosphine); oxygen-containing compounds such as tetrahydrofuran; and nitrogen-containing compounds such as $NH_3$ (ammine), NO, $NO_2$ (nitro), $NO_3$(nitrato), ethylenediamine, diethylenetriamine, pyridine, and phenanthroline. In a complex or a complex salt, the species of ligands may be the same or different from each other, and one species or more than two species of ligands may be coordinated therein.

As a preferable ligand in a complex, e. g., OH group, alkoxy groups, acyl groups, alkoxycarbonyl groups, acetylacetonato, cyclopentadienyl, $C_{1-2}$alkyl-substituted cyclopentadienyls, halogen atoms, CO, CN, $H_2O$ (aquo), phosphorous compounds such as triphenylphosphine, oxygen-containing compounds such as tetrahydrofuran (THF), or nitrogen-containing compounds inclusive of $NH_3$, $NO_2$ and $NO_3$ are usually employed. As a complex, there may be exemplified an acetylacetonato complex (e.g., acetylacetonato complexes of e.g., Ce, Ti, Zr, V, Cr, Mo, Mn, Fe, Ru, Co, Ni, Cu, or Zn; titanylacetylacetonato complex TiO(AA)$_2$; zirconylacetylacetonato complex ZrO(AA)$_2$; vanadylacetylacetonato complex VO(AA)$_2$; diacetylacetonatosamarium (II); triacetylacetonatosamarium (III)), cyano complexes (e.g., hexacyanomanganate (I), hexacyanocuprate (II)), carbonyl complexes and cyclopentadienyl complexes (e.g., samallocene-type complexes such as dicyclopentadienylsamarium (II), tricyclopentadienylsamarium (III), dipentamethylcyclopentadienylsamarium (II), and tripentamethylcyclopentadienylsamarium(III); tricarbonylcyclopentadienylmanganese (I), biscyclopentadienylmanganese (II), biscyclopentadienyliron (II), Fe(CO)$_5$, Fe$_2$(CO)$_9$, Fe$_3$(CO)$_{12}$); nitrosyl compounds (e.g., Fe(NO)$_4$, Fe(CO)$_2$(NO)$_2$); thiocyanato complexes (e.g., thiocyanatocobalt, thiocyanatomanganese, thiocyanatoiron), acetyl complexes (e.g., zirconyl acetate ZrO(OAc)$_2$, titanyl acetate TiO(OAc)$_2$, vanadyl acetate VO(OAc)$_2$), and other corresponding metal complexes.

A polyacid (e.g., isopolyacid and heteropolyacid) is usually at least one of, e.g., the group 5A elements or the group 6A elements of the Periodic Table of Elements, such as V (vanadic acid), Mo (molybdic acid) and W (tungstic acid). The central atom is not particularly restricted, and may be, e.g., Cu, Be, B, Al, Si, Ge, Sn, Ti, Th, N, P, As, Sb, V, Nb, Ta, Cr, Mo, W, S, Se, Te, Mn, I, Fe, Co, Ni, Rh, Os, Ir, Pt. As concrete examples of heteropolyacids or salts thereof, there may be mentioned phosphomolybdic acid, phosphotungstic acid, silicomolybdic acid, silicotungstic acid, cobaltmolybdic acid, cobalttungstic acid, molybdenumtungstic acid, manganesemolybdic acid, manganesetungstic acid, manganesemolybdenumtungstic acid, vanadomolybdophosphoric acid, phosphovanadomolybdic acid, manganesevanadiummolybdic acid, manganesevanadomolybdophosphoric acid, and salts thereof.

Further, as boron compounds, there may be exemplified boric acids (e.g., orthoboric acid, methaboric acid, tetraboric acid); borates (e.g., nickel borate, magnesium borate, manganese borate); boron oxides such as B$_2$O$_3$, nitrogen-containing compounds such as borazane, borazen, borazine, and boron amide; halides such as BF$_3$, BCl$_3$, and tetrafluoroborate; and boric esters (e.g., methyl borate, phenyl borate).

The metal catalyst may be a homogeneous or heterogeneous system. Further, the catalyst may be a solid catalyst in which a catalytic component is supported on a carrier. Porous carriers such as activated carbon, zeolites, silica, silica-alumina, bentonite are usually employed as the carrier. The amount of the catalytic component supported on the carrier is about 0.1 to 50 parts by weight, preferably about 0.5 to 30 parts by weight, and more preferably about 1 to 20 parts by weight, relative to 100 parts by weight of the carrier.

The catalyst is useful in producing an α-cyanohydrin ester derivative shown by the formula (3) by reacting an enol ester compound shown by the formula (1) with a carbonyl compound shown by the formula (2) and a cyanogenation agent.
[Enol ester compound (1)]

In an enol ester compound shown by the formula (1) (enol ester compound (1)), R$^1$ represents a non-reactive atom or a non-reactive organic group.

The non-reactive atom or non-reactive organic group includes, e.g., hydrogen atom, halogen atoms, alkyl groups, alkenyl groups, alkynyl group, aryl groups, cycloalkyl groups, and heterocyclic groups.

The halogen atoms include iodine, bromine, chlorine, and fluorine. Alkyl groups include linear or branched chain alkyl groups having about 1 to 20 carbon atoms (preferably, alkyl groups having about 1 to 10 carbon atoms), such as methyl, ethyl, propyl, isopropyl, butyl, isobutyl, s-butyl, t-butyl, pentyl, hexyl, heptyl, octyl, decyl, undecyl, dodecyl, tetradecyl, andoctadecyl groups. Preferred alkyl groups are, e. g., lower alkyl groups having about 1 to 6 carbon atoms, particularly about 1 to 4 carbon atoms.

The alkenyl groups include alkenyl groups having about 2 to 20 carbon atoms (preferably alkenyl groups having about 2 to 10 carbon atoms, particularly about 2 to 6 carbon atoms), such as vinyl, propenyl, 2-propenyl, butenyl, pentenyl, octenyl, and dodecyl group.

The alkynyl groups include alkynyl groups having about 2 to 20 carbon atoms (preferably alkynyl groups having about 2 to 10 carbon atoms, particularly 2 to 6 carbon atoms), such as ethynyl, propynyl, and octhynyl group.

The aryl groups include aryl groups having about 6 to 14 carbon atoms, such as phenyl group and naphthyl group. Cycloalkyl groups include cycloalkyl groups having about 3 to 10 carbon atoms, such as cyclopentyl, cyclohexyl, cycloheptyl, and cyclooctyl group.

Heterocycles corresponding to the heterocyclic groups include hyterocycles containing an oxygen atom as a heteroatom (e.g., 5-membered rings such as furan, oxazole, isooxazole, and tetrahydrofuran; 6-membered rings such as pyran; fused or condensed rings such as benzofuran, isobenzofuran, dibenzofuran, xanthone, xanthene, chroman, isochroman, and chromene), heterocycles containing a sulfur atom as a heteroatom (e.g., thiophene, thiazole, isothiazole, thiadiazole, benzothiophene), heterocycles containing a nitrogen atom as a heteroatom (e.g., 5-membered rings such as pyrrole, pyrazole, imidazole, triazole, and pyrrolidine; 6-membered rings such as pyridine, pyridazine, pyrimidine, pyrazine, piperidine, and morpholine; fused or condensed rings such as indole, indolene, isoindole, indazole, indoline, isoindoline, quinoline, isoquinoline, quinolinequinoline, quinoxaline, quinazoline, phthalazine, purine, carbazole, acridine, naphthoquinoline, phenanthrodine, phenanthroline, naphthyridine, benzoquinoline, phenoxazine, phthalocyanine, and anthracyanine.

R$^1$, representing any of the alkyl groups, alkenyl groups, alkynyl groups, aryl groups, cycloalkyl groups, and heterocyclic groups, may have a substituent. As a substituent, there may be exemplified hydroxyl group, mercapto group, carboxyl group, substituted-oxy groups (e.g., alkoxy group, aryloxy group), substituted-thio groups (e.g., alkylthio group, arylthio group), substituted-oxycarbonyl groups (e.g., alkoxycarbonyl group, aryloxycarbonyl group), oxo group, carbamoyl group, substituted-carbamoyl groups, cyano group, nitro group, amino group, substituted-amino groups, sulfo group, aromatic hydrocarbon groups, heterocyclic groups, halogen atoms, alkyl groups, alkenyl groups, alkynyl groups, and cycloalkyl groups.

Included as preferred R$^1$ are hydrogen atom, C$_{1-10}$alkyl groups (e.g., C$_{1-6}$alkyl groups, particularly C$_{1-4}$alkyl groups), C$_{2-10}$alkenyl groups (e.g., C$_{2-6}$alkenyl groups), C$_{6-10}$aryl groups (e.g., phenyl group), and C$_{3-10}$cycloalkyl groups (e.g., C$_{5-8}$cycloalkyl groups). Among them, e.g., hydrogen atom, methyl group, ethyl group, vinyl group, 2-propenyl group, and phenyl group are preferred as R$^1$. In the formula (1), as alkyl groups having 1 to 5 carbon atoms represented by R$^2$, R$^3$, and R$^4$, there may be exemplified methyl, ethyl, propyl, isopropyl, butyl, isobutyl, and pentyl group. At least two groups of R$^2$, R$^3$, and R$^4$, together with one or two adjacent carbon atoms, may bond together to form a ring. Examples of such ring are cycloalkane rings or cycloalkene rings such as cyclopropane ring, cyclobutane ring, cyclopentane ring, cyclohexane ring, cyclohexene ring, and cycloheptane ring. These are, e.g., about 3 to 10 membered rings.

$R^2$ is preferably a hydrogen atom or a $C_{1-3}$alkyl group, and more preferably a hydrogen atom. Each of $R^3$ and $R^4$ is preferably a hydrogen atom or a $C_{1-3}$alkyl group, and more preferably a hydrogen atom.

Preferred as an enol ester compound (1) are, e.g., vinyl formate, vinyl acetate, vinyl propionate, isopropenyl formate, isopropenyl acetate, and isopropenyl propionate.

[Oxime ester compound (2)]

In an oxime ester compound shown by the formula (2) (oxime ester compound (2)), as $R^1$, there may be mentioned groups similar to those exemplified above. Moreover, as non-reactive atoms and non-reactive organic groups represented by $R^5$ and $R^6$, any of the non-reactive atoms and non-reactive organic groups exemplified in connection with $R^1$ may be employed.

Preferred as $R^5$ and $R^6$ are, e.g., $C_{1-10}$alkyl groups (e.g., $C_{1-6}$alkyl groups), $C_{6-10}$aryl groups (e.g., phenyl group), and $C_{3-10}$cycloalkyl groups (e.g., $C_{5-8}$cycloalkyl groups). Moreover, $R^5$ and $R^6$, together with the adjacent carbon atom, may bond together to form a ring (e.g., 3 to 20-membered ring, preferably 3 to 16-membered ring, more preferably 3 to 12-membered ring, particularly 5 to 10-membered ring).

The oxime ester compound (2) can be obtained by, e.g., reacting the enol ester compound (1) with an oxime compound shown by the formula (6) in the presence of the metal catalyst (e.g., compounds containing a Group 3 element of the Periodic Table of Elements, such as samarium compounds).

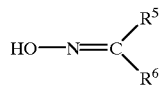

(6)

In the formula (6), $R^5$ and $R^6$ have the same meanings as defined above.

A compound corresponding to the oxime ester compound (2) is employed as an oxime compound shown by the formula (6) (oxime compound (6)). As the oxime compound (6), there may be exemplified aliphatic oximes such as 2-hexanone oxime; alicyclic oximes such as cyclohexanone oxime and cyclopentanone oxime; aromatic oximes such as acetophenone oxime, benzophenone oxime, and benzyl dioxime.

The reaction of the enol ester compound (1) with the oxime compound (6) is usually carried out in a solvent. As the solvent, there may be exemplified aromatic hydrocarbons such as benzene, toluene, xylene, and ethylbenzene; hydrocarbon halides such as carbon tetrachloride, chloroform, dichloromethane, and 1,2-dichloroethane; aliphatic hydrocarbons such as pentane, hexane, heptane, and octane; alicyclic hydrocarbons such as cyclohexane and methylcyclohexane; esters such as methyl acetate, ethyl acetate, isopropyl acetate, butyl acetate, amyl acetate, cellosolve acetate, and ethyl propionate; ethers such as diethyl ether, dibutyl ether, dioxane, and tetrahydrofuran; ketones such as acetone and methylethylketone; and non-protonic polar solvents such as acetonitrile, N,N-dimethylformamide, and dimethyl sulfoxide.

In the above reaction, the ratio of the enol ester compound (1) to the oxime compound (6) is, e.g., the former/the latter (molar ratio)=about 1/5 to 5/1, preferably about 1/2 to 2/1, more preferably about 1/1.5 to 1.5/1. Moreover, the amount of the metal catalyst used is, relative to 1 mole of the oxime compound (6), about 0.001 to 1 mole, preferably about 0.01 to 0.5 mole, and more preferably about 0.05 to 0.2 mole. The reaction temperature may be, e.g., about 0 to 100° C., preferably about 10 to 60° C., and more preferably about 10 to 40° C.

After the completion of the reaction, the oxime ester compound (2) is separated and purified by a conventional separation and purification method such as filtration, concentration, extraction, crystallization, recrystallization, and column chromatography.

[Carbonyl compound (3)]

The process of the present invention is applicable to a wide range of carbonyl compounds regardless of being aldehydes or ketones.

In a carbonyl compound shown by the formula (3) (carbonyl compound (3)), as non-reactive atoms or non-reactive organic groups represented by $R^7$ and $R^8$, there may be mentioned, e.g., the atoms and organic groups exemplified in connection with $R^1$. As a ring formed by $R^7$ and $R^8$ bound together with the adjacent carbon atom, there may be exemplified cycloalkane rings or cycloalkene rings such as cyclopropane ring, cyclobutane ring, cyclopentane ring, cyclohexane ring, cyclohexene ring, cycloheptane ring, cyclooctane ring, cyclodecane ring, and cyclododecane ring; and non-aromatic heterocycles containing 1 to 3 heteroatoms such as oxygen atom, sulfur atom and nitrogen atom. The ring is, e.g., about 3 to 20-membered, preferably about 3 to 16-membered, more preferably about 3 to 12-membered, and particularly about 5 to 10-membered ring.

Among the carbonyl compounds (3), as concrete examples of an aldehyde, there may be exemplified saturated aliphatic aldehydes having about 2 to 20 carbon atoms (preferably, 2 to 10) such as acetoaldehyde, propionaldehyde, butanal, 2-methylpropanal, pentanal, 3-methylbutanal, dimethylpropanal, hexanal, heptanal, octanal, decanal, dodecanal, and octadecanal; unsaturated aliphatic aldehydes having about 4 to 20 carbon atoms (preferably, 4 to 10) such as 3-butenal, and 3-octenal; alicyclic aldehydes having about 4 to 20 carbon atoms (preferably, 4 to 15) such as cyclopentanecarbaldehyde, cyclohexanecarbaldehyde, and cycloheptanecarbaldehyde; aromatic aldehydes having about 7 to 15 carbon atoms (preferably, 7 to 11) such as benzaldehyde, phenylacetaldehyde, and 3-phenylpropanal; hetero cyclic aldehydes having a 5- or 6-membered heterocycle having about 1 to 3 heteroatoms of at least one kind selected from oxygen atom, sulfur atom, and nitrogen atom or a condensed heterocycle in which a benzene ring or the like is condensed with the 5- or 6-membered heterocycle, such as 2-furancarbaldehyde, 2-furylacetoaldehyde, 2-thiophenecarbaldehyde, 2-thienylacetoaldehyde, 2-pyridinecarbaldehyde, 3-pyridinecarbaldehyde, 4-pyridinecarbaldehyde, 2-pyridylacetoaldehyde, 3-pyridylacetoaldehyde, 4-pyridylacetoaldehyde, and 3-(2-quinolyl)propanal.

Among the carbonyl compounds (3), as ketones, there may be exemplified saturated aliphatic ketones having about 3 to 15 carbon atoms (preferably, 3 to 10, particularly 3 to 8) such as acetone, methyl ethyl ketone, methyl propyl ketone, methyl isopropyl ketone, methyl butyl ketone, methyl isobutyl ketone, methyl pentyl ketone, and methyl isopentyl ketone; unsaturated aliphatic ketones having about 4 to 15 carbon atoms such as methyl vinyl keton, mesityl oxide, and methylheptenone; alicyclic ketons having about 3 to 20 carbon atoms (preferably, 3 to 16) such as cyclobutanone, cyclopentanone, cyclohexanone, and cyclododecanone; aromatic ketones having about 8 to 18 carbon atoms (preferably, 8 to 15) such as acetophenone, propiophenone, butyrophenone, velerophenone, dibenzyl ketone, and 2-acetonaphthone; and heterocyclic ketones having a 5- or 6-membered heterocycle having about 1 to 3 heteroatoms of at least one kind selected from oxygen atom, sulfur atom, and nitrogen atom, or a condensed heterocycle in which a benzene ring or the like is condensed with the 5- or 6-membered heterocycle, such as acetothienone, 2-acetofuron, 2-acetylpyridine, 3-acetylpyridine, 3-propionylpyridine, 4-acetylpyridine, and 3-acetylquinoline.

By varying the groups represented by $R^7$ and $R^8$, various corresponding α-cyanohydrin esters (and various α-hydroxy acids and salts thereof) can be produced.

[Cyanogenation agent]

As a cyanogenation agent, there may be employed a conventional cyanogenation agent used for cyanogenation reaction. For example, there may be mentioned hydrogen cyanide, metal cyanides, cyanohydrin compounds, acyl cyanides, and cyanogen halides. Metal cyanides include, e.g., cyanides of alkaline metals, such as sodium cyanide and potassium cyanide; cyanides of alkaline earth metals, such as calcium cyanide; and cyanides of transition metals, such as copper cyanide. Cyanohydrin compounds include a wide range of α-cyanohydrin compounds corresponding to aliphatic, alicyclic, or aromatic aldehydes or ketones. As typical examples of α-cyanohydrin compounds, there may be mentioned aliphatic α-cyanohydrins such as hydroxyacetonitrile, lactonitrile, acetone cyanohydrin, 2-hydroxybutanenitrile, 2-hydroxy-4-methylbutanenitrile, 2-hydroxy-3-methylbutanenitrile, 2-hydroxy-3-butenenitrile, 2-hydroxypentanenitrile, 2-hydroxyhexanenitrile, and 2-hydroxyoctanenitrile; alicyclic α-cyanohydrins such as 2-hydroxycyclohexaneacetonitrile and cyclopentanone cyanohydrin; and aromatic α-cyanohydrins such as mandelonitrile and 2-hydroxy-3-phenylbutanenitrile. Acyl cyanides include aliphatic acyl cyanides such as acetyl cyanide and propionyl cyanide; and aromatic acyl cyanides such as benzoyl cyanide. Cyanogen halides include chlorocyanogen and bromocyanogen.

Preferred as a cyanogenation agent are, e.g., hydrogen cyanide, metal cyanides, cyanohydrin compounds, and acyl cyanides. Among them, hydrogen cyanide, cyanides of alkaline metals, cyanohydrin compounds (especially, aliphatic α-cyanohydrins having about 3 to 8 carbon atoms), particularly α-cyanohydrins derived from ketones are preferred.

[Production of α-cyanohydrin esters]

In the process for producing an α-cyanohydrin ester of the present invention, the enol ester compound (1) or the oxime ester compound (2) is reacted with the carbonyl compound (3) and a cyanogenation agent in the presence of a metal catalyst.

This reaction may be conducted in the absence of a solvent, but usually conducted in the presence of a solvent. As a solvent, the solvents exemplified above may be employed.

The amount of the enol ester compound (1) or the oxime ester compound (2) is, relative to 1 mole of the carbonyl compound (3), e.g., about 0.5 to 5 mole, preferably about 0.8 to 4 mole, and more preferably about 1 to 3 mole (particularly, 1.5 to 2.5 mole). The amount of the cyanogenation agent used is, relative to 1 mole of the carbonyl compound (3), e.g., not less than 0.8 mole (e.g., about 0.8 to 5 mole), preferably about 0.8 to 3 mole, and more preferably about 0.9 to 1.5 mole.

The amount of the metal catalyst used is, relative to 1 mole of the carbonyl compound (3), e.g., about 0.001 to 1 mole, preferably about 0.01 to 0.5 mole, and more preferably about 0.05 to 0.2 mole. The reaction temperature is selected within the range not adversely affecting the reaction. For example, the reaction temperature is about 0 to 100° C., preferably 10 to 60° C., and more preferably about 10 to 40° C.

When employing an enol ester compound (1) as a reaction component, the oxime compound (6) may be present in the system. The presence of the oxime compound (6) in the system sometimes accelerates the reaction speed. In this case, the amount of the oxime compound (6) used may be selected within a wide range, and may be, e.g., about 0.001 to 2 mole and preferably about 0.01 to 0.5 mole relative to 1 mole of the carbonyl compound (3).

The reaction may be carried out in a conventional manner such as batch system, semi-batch system, and continuous system. As a result of the reaction above, an α-cyanohydrin ester derivative shown by the corresponding formula (4) is produced. After the completion of the reaction, a protonic compound such as water may be added to the reaction system, if necessary.

Since this reaction proceeds irreversibly, an α-cyanohydrin ester (4) can be obtained in high yield.

The produced α-cyanohydrin ester (4) can be separated and purified by a conventional separation and purification method, e.g., filtration, concentration, extraction, crystallization, recrystallization, column chromatography, or a combination of such methods.

Since the α-cyanohydrin ester (4) produced according to such process is different from α-cyanohydrins, and unsusceptible to an elimination reaction such as de-hydrogen cyanidation (elimination of hydrogen cyanide) under conditions of hydrolysis, it is useful as a precursor of an α-hydroxy acid.

[Production of an α-hydroxy acid or a salt thereof]

An α-hydroxy acid or a salt thereof can be obtained by hydrolyzing the α-cyanohydrin ester (4) obtained by the process described above.

The hydrolysis can be conducted by a conventional hydrolysis method, such as acid hydrolysis method and alkali hydrolysis method.

As acids that may be employed for acid hydrolysis, there may be exemplified inorganic acids such as hydrochloric acid, sulfuric acid, nitric acid, and phosphoric acid; and sulfonic acids such as methanesulfonic acid, ethanesulfonic acid, benzenesulfonic acid, and p-toluenesulfonic acid. The amount of the acid is, e.g., about 0.0001 to 10 mole, and preferably about 0.01 to 4 mole relative to 1 mole of the α-cyanohydrin ester (4).

The amount of water is, relative to 1 mole of the α-cyanohydrin ester (4), not less than 1 mole, and suitably selected within the range of about 1 to 100 mole. Hydrolysis may be conducted in the presence of an organic solvent, provided it doesn't affect the reaction. Exemplified as the organic solvent are the solvents mentioned above. The reaction temperature is, e.g., about 0 to 150° C., preferably about 10 to 110°, and more preferably about 40 to 100° C.

Usually, the acid hydrolysis of the α-cyanohydrin ester (4) provides a free α-hydroxy acid or an ammonium salt thereof. These products can be converted to basic salts of α-hydroxy acids by a conventional method.

The alkali hydrolysis is carried out in the presence of a base. As the base, there may be exemplified hydroxides of alkaline metals, such as lithium hydroxide, sodium hydroxide, and potassium hydroxide; hydroxides of alkaline earth metals, such as magnesium hydroxide, calcium hydroxide, and barium hydroxide; carbonates of alkaline metals, such as sodium carbonate and potassium carbonate; carbonates of alkaline earth metals such as magnesium carbonate; and hydrogencarbonates of alkaline metals, such as sodium hydrogencarbonate and potassium hydrogencarbonate.

The amount of the basis is, relative to 1 mole of the α-cyanohydrin ester (4), not less than 1 mole, e.g., about 1 to 10 mole, preferably about 1 to 5 mole, and more preferably about 2 to 3 mole. The amount of water is similar to those exemplified in the paragraphs referring to acid hydrolysis, and the reaction may be-conducted in the presence of any of the aforementioned organic solvents or alcohols (e.g., methanol, ethanol). The reaction temperature is, e.g., about 0 to 150° C., and preferably about 10 to 110° C.

Usually, the alkaline hydrolysis of the α-cyanohydrin ester (4) provides a basic salt of the corresponding α-hydroxy acid. The basic salt of the α-hydroxy acid can be converted to a free α-hydroxy acid or an acid salt thereof by a conventional method.

The hydrolysis reaction may be conducted by a conventional method such as batch system, semi-batch system, and continuous system. After the completion of the reaction, the pH is adjusted, if need be, and then the reaction product is easily separated and purified by a conventional separation method, e.g., filtration, concentration, distillation, extraction, crystallization, recrystallization, column chromatography, and a combination of these methods.

INDUSTRIAL APPLICABILITY

According to the present invention, an α-cyanohydrin ester in high yield can be obtained from an enol ester compound or an oxime ester compound, a carbonyl compound, and a cyanogenation agent.

Moreover, by hydrolyzing the α-cyanohydrin ester, the corresponding α-hydroxy acid or a salt thereof can be produced in high yield. This process is of broader applicability and general-purpose.

EXAMPLES

The following examples are intended to describe the present invention in further detail and should by no means be interpreted as defining the scope of the invention.

Preparation Example 1

A mixture of 2.3 g (20 mmole) of cyclohexanone oxime, 2.0 g (20 mmole) of isopropenyl acetate, 0.9 g (2 mmole) of di($\eta^5$-pentamethylcyclopentadienyl)samarium [Cp*$_2$Sm(THF)$_2$], and 20 ml of toluene was stirred at room temperature for one hour, and the precipitated crystals were filtered. 3.1 g of acetyloxyiminocyclohexane (cyclohexanone oxime acetate) (yield: 100%) was obtained.

Example 1

A mixture of 1 mmole of isopropenyl acetate, 1 mmole of propanal, 1 mmole of acetone cyanohydrin, 0.1 mmole of di($\eta^5$-pentamethylcyclopentadienyl)samarium [Cp*$_2$Sm(THF)$_2$], and 1 ml of toluene was stirred at a temperature of 50° C. for 5 hours. The analysis by a gas chromatography revealed that 2-acetyloxybutanenitrile was formed in the reaction mixture in a 73% yield. The conversion of propanal was 79%.

Example 2

The reaction was conducted in the same manner as directed in Example 1 except for the use of 1 mmol of butanal instead of propanal. The conversion of butanal was 86%, and 2-acetyloxypentanenitrile was formed in an 81% yield.

Example 3

The reaction was conducted in the same manner as Example 1 except for the use of 1 mmole of pentanal instead of propanal. The conversion of pentanal was 86%, and 2-acetyloxyhexanenitrile was formed in an 80% yield.

Example 4

The reaction was conducted in the same manner as Example 1 except for the use of 1 mmol of hexanal instead of propanal. The conversion of hexanal was 86%, and 2-acetyloxyheptanenitrile was formed in an 81% yield.

Example 5

The reaction was conducted in the same manner as Example 1 except for the use of 1 mmole of 3-methylbutanal instead of propanal. The conversion of 3-methylbutanal was 84%, and 2-acetyloxy-4-methylpentanenitrile was formed in a 79% yield.

Example 6

The reaction was conducted in the same manner as Example 1 except for the use of 1 mmole of 2-phenylacetaldehyde instead of propanal. The conversion of 2-phenylacetaldehyde was 78%, and 2-acetyloxy-3-phenylpropanenitrile was formed in a 72% yield.

Example 7

The reaction was conducted in the same manner as Example 1 except for the use of 1 mmole of acetaldehyde instead of propanal. The conversion of 2-phenylacetaldehyde was 81%, and 2-acetyloxypropanenitrile was formed in a 74% yield.

Example 8

The reaction was conducted in the same manner as Example 1 except for the use of 0.1 mmole of aluminium chloride anhydride (AlCl$_3$) instead of di($\eta^5$-pentamethylcyclopentadienyl)samarium [Cp*$_2$Sm(THF)$_2$]. The conversion of propanal was 87%, and 2-acetyloxybutanenitrile was formed in an 81% yield.

Example 9

The reaction was conducted in the same manner as Example 1 except for the use of 0.1 mmole of zirconyl chloride (ZrOCl$_2$) instead of di($\eta^5$-pentamethylcyclopentadienyl)samarium [Cp*$_2$Sm(THF)$_2$]. The conversion of propanal was 77%, and 2-acetyloxybutanenitrile was formed in a 74% yield.

Example 10

The reaction was conducted in the same manner as Example 1 except for the use of 0.1 mmole of titanium tetrachloride (TiCl$_4$) instead of di($\eta^5$-pentamethylcyclopentadienyl)samarium [Cp*$_2$Sm(THF)$_2$]. The conversion of propanal was 81%, and 2-acetyloxybutanenitrile was formed in a 77%.

Example 11

The reaction was conducted in the same manner as Example 1 except for the use of 0.1 mmole of acetylacetonatozinc [Zn(AA)$_2$] instead of di($\eta^5$-pentamethylcyclopentadienyl)samarium [Cp*$_2$Sm(THF)$_2$]. The conversion of propanal was 66%, and 2-acetyloxybutanenitrile was formed in a 62% yield.

Example 12

The reaction was conducted in the same manner as Example 1 except for the use of 0.1 mole of copper chloride [Cu(Cl)$_2$)] instead of di($\eta^5$-pentamethylcyclopentadienyl) samarium [Cp*$_2$Sm(THF)$_2$]. The conversion of propanal was 58%, and 2-acetyloxybutanenitrile was formed in a 56% yield.

Example 13

The reaction was conduced in the same manner as Example 1 except for the use of 0.1 mmole of ferric chloride [Fe(Cl)$_3$] instead of di($\eta^5$-pentamethylcyclopentadienyl) samarium [Cp*$_2$Sm(THF)$_2$]. The conversion of propanal was 55%, and 2-acetyloxybutanenitrile was formed in a 53% yield.

Example 14

The reaction was conducted in the same manner as Example 1 except for the use of 0.1 mmole of vanadyl chloride (VOCl$_2$) instead of di($\eta^5$-pentamethylcyclopentadienyl)samarium [Cp*$_2$Sm(THF)$_2$]. The conversion of propanal was 78%, and 2-acetyloxybutanenitrile was formed in a 72% yield.

Example 15

The reaction was conducted in the same manner as Example 1 except for the use of 0.1 mmole of molybdenum chloride [Mo(Cl)$_3$] instead of di($\eta^5$-pentamethylcyclopentadienyl)samarium [Cp*$_2$Sm(THF)$_2$]. The conversion of propanal was 72%, and 2-acetyloxybutanenitrile was formed in a 70% yield.

Example 16

The reaction was conducted in the same manner as Example 2 except for the reaction temperature and the reaction time varied to 25° C. and 3 hours, respectively. 2-acetyloxypentanenitrile was formed in a 56% yield.

Example 17

The reaction was conducted in the same manner as Example 2 except for the reaction temperature and reaction time varied to 25° C. and 15 hours, respectively. 2-acetyloxypentanenitrile was formed in a 63% yield.

Example 18

The reaction was conducted in the same manner as Example 2 except for the use of 0.1 mmole of di($\eta^5$-pentamethylcyclopentadienyl)ytterbium [Cp*$_2$Yb(THF)$_2$] instead of di($\eta^5$-pentamethylcyclopentadienyl)samarium [Cp*$_2$Sm(THF)$_2$] and for the reaction temperature and reaction time varied to 25° C. and 3 hours, respectively. 2-acetyloxypentanenitrile was formed in a 21% yield.

Example 19

The reaction was conducted in the same manner as Example 2 except for the use of 0.1 mmole of samarium isopropoxide [Sm(O-i-Pr)$_3$] instead of di($\eta^5$-pentamethylcyclopentadienyl)samarium [Cp*$_2$Sm(THF)$_2$] and for the reaction temperature and reaction time varied to 25° C. and 3 hours, respectively. 2-acetyloxypentanenitrile was formed in a 61% yield.

Example 20

The reaction was conducted in the same manner as Example 2 except for the use of 0.1 mmole of samarium isopropoxide [Sm(O-i-Pr)$_3$] instead of di($\eta^5$-pentamethylcyclopentadienyl)samarium [Cp*$_2$Sm(THF)$_2$] and for the reaction temperature and reaction time varied to 25° C. and 15 hours, respectively. 2-acetyloxypentanenitrile was formed in a 70% yield.

Example 21

A mixture of 2 mmole of ispropenyl acetate, 1 mmole of acetaldehyde, 1 mmole of acetone cyanohydrin, 0.1 mmole of di($\eta^5$-pentamethylcyclopentadienyl)samarium [Cp*$_2$Sm (THF)$_2$], and 1 ml of toluene was stirred at 25° C. for 15 hours. The analysis by gas chromatography revealed that 2-acetyloxypropanenitrile was formed in the reaction mixture in a 74% yield.

Example 22

The reaction was conducted in the same manner as Example 21 except for the use of 1 mmole of propanal instead of acetaldehyde. 2-acetyloxybutanenitrile was formed in a 87% yield.

Example 23

The reaction was conducted in the same manner as Example 21 except for the use of 1 mmole of butanal instead of acetaldehyde. 2-acetyloxypentanenitrile was formed in a 84% yield.

Example 24

The reaction was conducted in the same manner as Example 21 except for the use of 1 mmole of 2-methylpropanal instead of acetaldehyde. 2-acetyloxy-3-methylbutanenitrile was formed in a 86% yield.

Example 25

The reaction was conducted in the same manner as Example 21 except for the use of 1 mmole of 3-methylbutanal instead of acetaldehyde. 2-acetyloxy-4-methylpentanenitrile was formed in a 82% yield.

Example 26

The reaction was conducted in the same manner as Example 21 except for the use of 1 mmole of 2,2-dimethylpropanal and 0.1 mmole of samarium isopropoxide [Sm(O-i-Pr)$_3$] instead of acetaldehyde and di($\eta^5$-pentamethylcyclopentadienyl)samarium [Cp*$_2$Sm(THF)$_2$], respectively. 2-acetyloxy-3,3-dimethylbutanenitrile was formed in a 83% yield.

Example 27

The reaction was conducted in the same manner as directed in Example 21 except for the use of 1 mmole of cyclohexanecarbaldehyde instead of acetaldehyde. 2-acetyloxy-2-cyclohexylethanenitrile in a 90% yield.

Example 28

The reaction was conducted in the same manner as Example 21 except for the use of 1 mmole of benzaldehyde instead of acetaldehyde. 2-acetyloxy-3-phenylethanenitrile was formed in a 49% yield.

Example 29

The reaction was conducted in the same manner as Example 21 except for the use of 1 mmole of phenylacetaldehyde instead of acetaldehyde. 2-acetyloxy-3-phenylpropanenitrile was formed in a 67% yield.

Example 30

The reaction was conducted in the same manner as Example 21 except for the use of 1 mmole of 2-furancarbaldehyde instead of acetaldehyde. 2-acetyloxy-2-(2-furyl)ethanenitrile was formed in an 18% yield.

Example 31

The reaction was conducted in the same manner as Example 21 except for the use of 1 mmole of cyclohexanone instead of acetaldehyde and the reaction temperature varied to 50° C. 1-acetyloxycyclohexanenitrile was formed in a 13% yield.

Example 32

A mixture of 1 mmole of the acetyloxyiminocyclohexane obtained in the Preparation Example 1, 1 mmole of butanal, 1 mmole of acetone cyanohydrin, 0.1 mmole of di($\eta^5$-pentamethylcyclopentadienyl)samarium [Cp*$_2$Sm(THF)$_2$], and 1 ml of toluene was stirred at 25° C. for 3 hours. The analysis by a gas chromatography revealed that 2-acetloxypentanenitrile was formed in the reaction mixture in a 51% yield.

Example 33

A mixture of 10 mmole of 2-acetyloxybutanenitrile obtained in the same manner as Example 1, 20 mmole of potassium hydroxide, 5 ml of water and 10 ml of ethanol was stirred at 60° C. for 3 hours. The analysis of the reaction mixture by a high performance liquid chromatography revealed the formation of 2-hydroxybutanoic acid in an 86% yield.

Example 34

The reaction was conducted in the same manner as Example 33 except for the use of 10 mmole of 2-acetyloxypentanenitrile obtained in the same manner as Example 2 instead of 2-acetyloxybutanenitrile. 2-hydroxypentanoic acid was formed in a 78% yield.

Example 35

The reaction was conducted in the same manner as Example 33 except for the use of 10 mmole of 2-acetyloxyhexanenitrile obtained in the same manner as Example 3 instead of 2-acetyloxybutanenitrile. 2-hydroxyhexanoic acid was formed in an 82% yield.

Example 36

The reaction was conducted in the same manner as Example 33 except for the use of 10 mmole of 2-acetyloxyheptanenitrile obtained in the same manner as Example 4 instead of 2-acetyloxybutanenitrile. 2-hydroxyheptanoic acid was formed in a 77% yield.

Example 37

The reaction was conducted in the same manner as Example 33 except for the use of 10 mmole of 2-acetyloxy-4-methylpentanenitrile obtained in the same manner as Example 5 instead of 2-acetyloxybutanenitrile. 2-hydroxy-4-methylpentanoic acid was formed in an 81% yield.

Example 38

The reaction was conducted in the same manner as Example 6 except for the use of 10 mmole of 2-acetyloxy-3-phenylpropanenitrile obtained in the same manner as Example 33 instead of 2-acetyloxybutanenitrile. 2-hydroxy-3-phenylpropionic acid was formed in a 78% yield.

Example 39

The reaction was conducted in the same manner as Example 33 except for the use of 10 mmole of 2-acetyloxypropanenitrile obtained in the same manner as Example 7 instead of 2-acetyloxybutanenitrile. 2-hydroxypropionic acid was formed in an 84% yield.

What is claimed is:

1. A process for producing an α-cyanohydrin ester, which comprises, in the presence of a metal catalyst, reacting an enol ester compound shown by the formula (1):

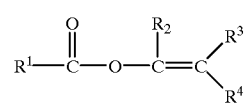

(1)

wherein $R^1$ represents a non-reactive atom or a non-reactive group; $R^2$, $R^3$, and $R^4$ are the same or different from each other and each represents a hydrogen atom or an alkyl group having 1 to 5 carbon atoms; and $R^2$, $R^3$, and $R^4$, together with 1 or 2 adjacent carbon atoms, may bond together to form a ring or an oxime ester compound shown by the formula (2):

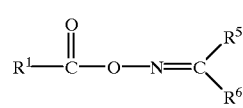

(2)

wherein $R^5$ and $R^6$ are the same or different from each other and each represents a non-reactive atom or a non-reactive organic group; $R^5$ and $R^6$, together with the adjacent carbon atom, may bond together to form a ring; and $R^1$ has the same meaning as defined above with a carbonyl compound shown by the formula (3):

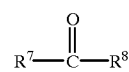

(3)

wherein $R^7$ and $R^8$ are the same or different from each other and each represents a non-reactive atom or a non-reactive organic group; and $R^7$ and $R^8$, together with the adjacent carbon atom, may bond together to form a ring and a cyanogenation agent
to form an α-cyanohydrin ester shown by the formula (4):

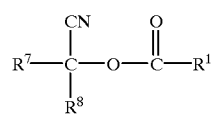
(4)

wherein $R^1$, $R^7$, and $R^8$ have the same meaning as defined above.

2. A process for producing an α-cyanohydrin ester according to claim 1, wherein a transition metal compound is employed as said metal catalyst.

3. A process for producing an α-cyanohydrin ester according to claim 1, wherein said metal catalyst comprises at least one element selected from the group consisting of the group 3A elements, the Group 4A elements, the group 5A elements, the groups 6A elements, the Group 7A elements, the Group 8 elements, the Group 1B elements, the Group 2B elements, and the Group 3B elements of the Periodic Table of Elements.

4. A process for producing an α-cyanohydrin ester according to claim 1, wherein $R^1$ is a group selected from hydrogen atom, $C_{1-10}$alkyl groups, $C_{2-10}$alkenyl groups, $C_{3-10}$cycloalkyl groups, and $C_{6-10}$aryl groups.

5. A process for producing an α-cyanohydrin ester according to claim 1, wherein $R^2$, $R^3$, and $R^4$ are the same or different from each other and each represents a hydrogen atom or a $C_{1-3}$alkyl group.

6. A process for producing an α-cyanohydrin ester according to claim 1, wherein $R^5$ and $R^6$ are the same or different from each other and are groups selected from $C_{1-10}$alkyl groups, $C_{3-10}$cycloalkyl groups, and $C_{6-10}$aryl groups, or form a 3- to 20-membered cycloalkane ring together with the adjacent carbon atom.

7. A process for producing an α-cyanohydrin ester according to claim 1, wherein said oxime ester compound (2) can be obtained by reacting, in the presence of said metal catalyst, said enol ester compound (1) with an oxime compound shown by the following formula (6):

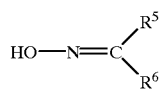
(6)

wherein $R^5$ and $R^6$ have the same meanings as defined above.

8. A process for producing an α-cyanohydrin ester according to claim 1, wherein said cyanogenation agent is a cyanogen compound selected from hydrogen cyanide, metal cyanides, cyanohydrin compounds, and acyl cyanides.

9. A process for producing an α-cyanohydrin ester according to claim 1, wherein said cyanogenation agent is a compound selected from hydrogen cyanide, cyanides of alkali metals and aliphatic α-cyanohydrins having 3 to 8 carbon atoms.

10. A process for producing an α-cyanohydrin ester according to claim 1, wherein the amount of said enol ester compound (1) or said oxime ester compound (2) is 0.5 to 5 mole relative to 1 mole of said carbonyl compound (3).

11. A process for producing an α-cyanohydrin ester according to claim 1, wherein the amount of said cyanogenation agent is not less than 0.8 mole relative to 1 mole of said carbonyl compound (3).

12. A process for producing an α-cyanohydrin ester according to claim 1, wherein the amount of said metal catalyst is 0.001 to 1 mole relative to 1 mole of said carbonyl compound (3).

13. A process for producing an α-cyanohydrin ester, which comprises, in the presence of a metal catalyst,
reacting an enol ester compound shown by the formula (1):

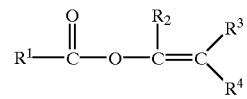
(1)

wherein $R^1$ represents a hydrogen atom, a $C_{1-6}$alkyl group, a $C_{2-6}$alkeny group, a $C_{6-10}$aryl group, or a $C_{5-8}$cycloalkyl group; $R^2$ represents a hydrogen atom or methyl group; and $R^3$ and $R^4$ represent hydrogen atoms
or an oxime ester compound shown by the formula (2):

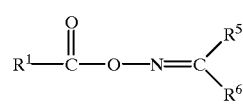
(2)

wherein $R^5$ and $R^6$ are the same or different from each other and each represents a $C_{1-6}$alkyl group, a $C_{6-10}$aryl group, or a $C_{5-8}$cycloalkyl group; $R^5$ and $R^6$, together with the adjacent carbon atom, may bond together to form a 3- to 16-membered ring; and $R^1$ has the same meaning as defined above
with a carbonyl compound shown by the formula (3):

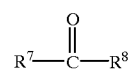
(3)

wherein $R^7$ and $R^8$ are the same or different from each other and each represents a hydrogen atom, a $C_{1-6}$alkyl group, $C_{2-6}$alkenyl group, $C_{6-10}$aryl group, or a $C_{5-8}$cycloalkyl group; and $R^7$ and $R^8$, together with the adjacent carbon atom, may bond together to form a 3- to 16-membered ring
and a cyanogenation agent
to form an α-cyanohydrin ester shown by the formula (4):

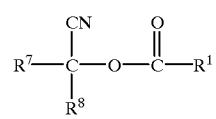
(4)

wherein $R^1$, $R^7$, and $R^8$ have the same meaning as defined above.

14. A process for producing an α-cyanohydrin ester according to claim 13, wherein the amount of said enol ester compound (1) or said oxime ester compound (2) is 0.8 to 4 mole, the amount of said cyanogenation agent is 0.8 to 5 mole, and the amount of said metal catalyst is 0.01 to 0.5 mole, relative to 1 mole of said carbonyl compound (3).

15. A process for producing an α-hydroxy acid or a salt thereof, which comprises (a) hydrolyzing an α-cyanohydrin ester shown by the formula (4):

(4)

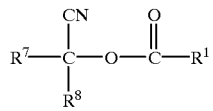

wherein $R^1$, $R^7$ and $R^8$ are the same or different from each other and each represents a non-reactive atom or a non-reactive organic group; and $R^7$ and $R^8$, together with the adjacent carbon atom, may bond together to form a ring, wherein said α-cyanohydrin ester of the formula (4) is produced by a process which comprises, (i) reacting in the presence of a metal catalyst, an enol ester compound shown by the formula (1):

(1)

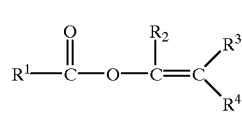

wherein $R^1$ represents a non-reactive atom or a non-reactive group; $R^2$, $R^3$ and $R^4$ are the same or different from each other and each represents a hydrogen atom or an alkyl group having 1 to 5 carbon atoms; and $R^2$, $R^3$ and $R^4$, together with 1 or 2 adjacent carbon atoms, may bond together to form a ring or an oxime ester compound shown by the formula (2):

(2)

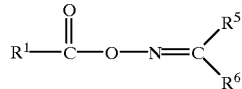

wherein $R^5$ and $R^6$ are the same or different from each other and each represents a non-reactive atom or a non-reactive organic group; $R^5$ and $R^6$, together with the adjacent carbon atom, may bond together to form a ring; and $R^1$ has the same meaning as defined above, (ii) with a carbonyl compound shown by the formula (3):

(3)

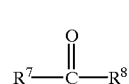

wherein $R^7$ and $R^8$ are the same or different from each other and each represents a non-reactive atom or a non-reactive organic group; and $R^7$ and $R^8$, together with the adjacent carbon atom, may bond together to form a ring, and (iii) a cyanogenation agent to form said α-cyanohydrin ester shown by the formula (4):

(4)

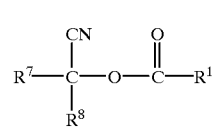

wherein $R^1$, $R^7$ and $R^8$ have the same meaning as defined above, to form an α-hydroxy acid shown by the formula (5):

(5)

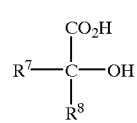

wherein $R^7$ and $R^8$ have the same meaning as defined above or a salt thereof.

* * * * *